United States Patent [19]

Annen et al.

[11] Patent Number: 4,587,236
[45] Date of Patent: May 6, 1986

[54] NOVEL 6α-METHYLPREDNISOLONE DERIVATIVES, THEIR PREPARATION, AND THEIR USE

[75] Inventors: Klaus Annen; Karl Petzoldt; Henry Laurent; Rudolf Wiechert; Helmut Hofmeister, all of Berlin, Fed. Rep. of Germany

[73] Assignee: Schering Aktiengesellschaft, Berlin and Bergkamen, Fed. Rep. of Germany

[21] Appl. No.: 546,143

[22] Filed: Oct. 27, 1983

Related U.S. Application Data

[63] Continuation of Ser. No. 409,264, Aug. 18, 1982, abandoned.

[30] Foreign Application Priority Data

Aug. 18, 1981 [DE] Fed. Rep. of Germany ....... 3133081

[51] Int. Cl.[4] .............................................. A61K 31/56
[52] U.S. Cl. ................................ 514/179; 260/397.45; 260/239.55 D
[58] Field of Search .................... 260/397.45; 424/243; 514/179

[56] References Cited

U.S. PATENT DOCUMENTS

| | | | |
|---|---|---|---|
| 2,867,632 | 1/1959 | Lincoln, Jr. et al. | 260/397.45 |
| 2,897,218 | 7/1959 | Sebek et al. | |
| 3,053,832 | 9/1962 | Gould. | |
| 3,312,590 | 4/1967 | Elks et al. | 260/397.45 |
| 3,422,193 | 1/1969 | Shapiro | 260/397.45 |
| 4,290,962 | 9/1981 | Tachi et al. | 260/397.45 |

FOREIGN PATENT DOCUMENTS

| | | | |
|---|---|---|---|
| 0072200 | 2/1983 | European Pat. Off. | 260/397.45 |
| 0095894 | 12/1983 | European Pat. Off. | 260/397.45 |
| 2144405 | 3/1973 | Fed. Rep. of Germany | 260/397.45 |

OTHER PUBLICATIONS

J. Amer. Chem. Soc., 78, 1956, 6213.
J. Amer. Chem. Soc., 81, 1959, 1235.
European Search Report, dated Nov. 3, 1982, No. EP 82 10 7368.
Apendice ao "Diario da Republica", pp. 1643, 2082-2083.
Anlage F—Pharmakologische Tests, 4 pages (German language).
Enclosure F—Pharmacological Tests, 4 pages (English language).
Early Disclosure Patent Gazette, No. 81-86119, Jul. 13, 1981, 11 pages.

Primary Examiner—Elbert L. Roberts
Attorney, Agent, or Firm—Millen & White

[57] ABSTRACT

6α-Methylprednisolone derivatives of Formula I

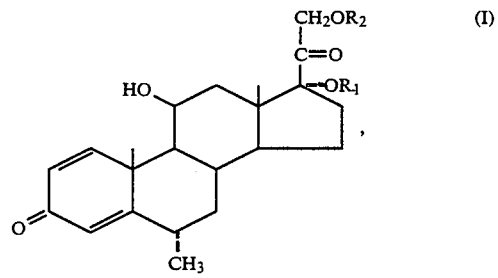

wherein
$R_1$ is 1-oxoalkyl of 2-6 carbon atoms or benzoyl and
$R_2$ is 1-oxoalkyl of 2-6 carbon atoms, are pharmacologically efficacious compounds, e.g., as antiinflammatories.

14 Claims, No Drawings

NOVEL 6α-METHYLPREDNISOLONE DERIVATIVES, THEIR PREPARATION, AND THEIR USE

This is a continuation of application Ser. No. 409,264 filed Aug. 18, 1982, now abandoned.

This invention relates to new pharmacologically active prednisolones.

SUMMARY OF THE INVENTION

It is an object of this invention to provide new antinflammatorily active agents, e.g.. especially topical agents.

Upon further study of the specification and appended claims, further objects and advantages of this invention will become apparent to those skilled in the art.

These objects have been attained by providing 6α-methylprednisolone derivatives of Formula I

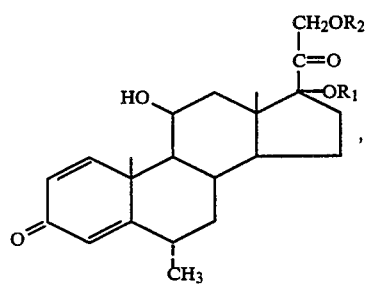

wherein
$R_1$ is 1-oxoalkyl of 2-6 carbon atoms or benzoyl, and
$R_2$ is 1-oxoalkyl of 2-6 atoms.

DETAILED DISCUSSION

In the novel 6α-methylprednisolone derivatives of Formula I, suitable 1-oxoalkyl (i.e., alkanoyl) groups for $R_1$ and $R_2$ are of 2-6 carbon atoms and include for example acetyl, propionyl, butyryl, isobutyryl, valeryl, 3-methylbutyryl, trimethylacetyl, hexanoyl, etc.

It has been found that the 6α-methylprednisolone derivatives of this invention surprisingly exhibit upon topical administration a significantly stronger antiinflammatory activity than the previously known derivatives of 6α-methylprednisolone. This activity often is even significantly stronger than that of difluorinated "thoroughbred corticoids" such as, for example, 6α,9α-difluoro-11β-hydroxy-16α-methyl-21-valeryloxy-1,4-pregnadiene-3,20-dione (="Nerisona").

Upon systemic administration, these derivatives of 6α-methylprednisolone surprisingly are less effective than the corresponding, previously known derivatives of 6α-methylprednisolone. (J. Amer. Chem. Soc., 78, 1956, 6213 and 81, 1959, 1235; U.S. Pat. Nos. 2,897,218 and 3,053,832).

The novel 6α-methylprednisolone derivatives of Formula I are accordingly suitable, in combination with the excipients customary and well known in galenic pharmacy, for the local treatment of contact dermatitis, eczemas of a great variety of types, neurodermatoses, erythrodermia, burns, pruritus vulvae et ani, rosacea, erythematodes cutaneus, psoriasis, lichen ruber planus et verrucosus, and similar skin disorders.

The drug specialties containing them are prepared in the usual way by bringing the active agents into the desired form of administration together with suitable additives, e.g., solutions, lotions, ointments, creams, or plasters. In the thus-formulated medicines, the active agent concentration is dependent on the form of administration. In case of lotions and ointments, an active agent concentration of 0.001% to 1% is preferably utilized.

Moreover, the novel compounds, optionally in combination with the usual excipients and adjuvants, are also well suited for the preparation of inhalants usable for therapy of allergic diseases of the respiratory tract, e.g. bronchial asthma or rhinitis.

Furthermore, the novel corticoids are also suitable, in the form of capsules, tablets, or dragees, preferably containing 10-200 mg of active ingredient and orally administered, or in the form of suspensions, preferably containing 100-500 mg of active ingredient per dosage unit and rectally administered, for the treatment of allergic diseases of the intestinal tract, such as colitis ulcerosa and colitis granulomatosa.

In all of these uses, the compound can be administered analogously to conventional steroidal agents used for the same purposes, such as, the known prednisolones.

The novel 6α-methylprednisolone derivatives of this invention can be prepared, under conditions described, e.g., in German Patent Applications Nos. 26 45 104; 26 45 105; 23 40 591, and 19 58 549, BP No. 1,131,146, BP No. 1,440,063, South African Pat. Nos. 7,705,915 and 7,705,914, and in U.S. Pat. No. 3,383,394, all of whose disclosures are incorporated by reference herein, e.g., by (a) conventionally esterifying a 6α-methylprednisolone-17-acylate of Formula II

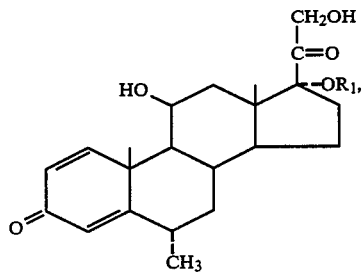

wherein $R_1$ is as defined above, in the 21-position with an alkanecarboxylic acid of 2-6 carbon atoms or with a conventional reactive derivative thereof, or (b) conventionally etherifying a 6α-methylprednisolone-21-acylate of Formula III

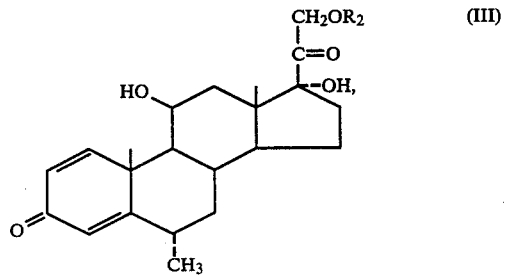

wherein $R_2$ is as defined above, in the 11-position with a trialkylsilyl compound or esterifying it with a derivative of a strongly acidic monocarboxylic acid; subsequently acylating the 17-position with a carboxylic acid chloride or carboxylic acid anhydride in the presence of 4-dimethylaminopyridine, and then splitting off the blocking group in the 11-position.

See, also, U.S. application Ser. No. 334,026, filed Dec. 23, 1981.

All the starting materials are well known or conventionally preparable by routine conventional procedures.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLE 1

A solution of 1.0 g of 17-acetoxy-11$\beta$,21-dihydroxy-6$\alpha$-methyl-1,4-pregnadiene-3,20-dione in 10 ml of pyridine is stirred with 5 ml of acetic anhydride for one hour at 0° C. Then the mixture is poured on an ice water-sodium chloride solution; the precipitate is filtered off and purified by crystallization from acetone/hexane, thus isolating 810 mg of 17,21-diacetoxy-11$\beta$-hydroxy-6$\alpha$-methyl-1,4-pregnadiene-3,20-dione, mp 216° C.

EXAMPLE 2

(a) 10.0 g of 11$\beta$,17,21-trihydroxy-6$\alpha$-methyl-1,4-pregnadiene-3,20-dione and 1.0 g of pyridinium tosylate are dissolved in 80 ml of dimethylformamide and 700 ml of benzene. At a bath temperature of 140° C., 300 ml of benzene is distilled off by way of a water trap; the solution is briefly cooled to 80° C. and combined with 24 ml of the triethyl ester of orthopropionic acid. Within 20 minutes, the residual benzene is distilled off together with the readily volatile solvent components. After adding 12 ml of pyridine, the mixture is concentrated under vacuum, thus obtaining 17,21-(1-ethoxypropylidenedioxy)-11$\beta$-hydroxy-6$\alpha$-methyl-1,4-pregnadiene-3,20-dione as an oil.

(b) A suspension of the above crude product in 300 ml of methanol is refluxed with a mixture of 12 ml of 0.1-molar aqueous sodium acetate solution and 108 ml of 0.1N aqueous acetic acid for 2.5 hours at 100° C. The mixture is concentrated until turbidity occurs, poured on water, and extracted with a large amount of ethyl acetate. The organic phase is washed with water, dried over sodium sulfate, and evaporated to dryness under vacuum. The crude product is purified on 600 g of silica gel with a methylene chloride-acetone gradient (0–12% acetone). Yield: 8.9 g of 11$\beta$,21-dihydroxy-6$\alpha$-methyl-17-propionyloxy-1,4-pregnadiene-3,20-dione, mp 214° C.

(c) Analogously to Example 1, 1.0 g of 11$\beta$,21-dihydroxy-6$\alpha$-methyl-17-propionyloxy-1,4-pregnadiene-3,20-dione is stirred in 10 ml of pyridine with 5 ml of acetic anhydride for one hour at room temperature and then worked up, thus isolating 790 mg of 21-acetoxy-11$\beta$-hydroxy-6$\alpha$-methyl-17-propionyloxy-1,4-pregnadiene-3,20-dione, mp 138° C.

EXAMPLE 3

Analogously to Example 1, 1.0 g of 11$\beta$,21-dihydroxy-6$\alpha$-methyl-17-propionyloxy-1,4-pregnadiene-3,20-dione in 10 ml of pyridine is treated with 5 ml of propionic anhydride and worked up. The crude product is purified on 100 g of silica gel with a methylene chloride-acetone gradient (0-12% acetone),thus isolating 760 mg of 11$\beta$-hydroxy-6$\alpha$-methyl-17,21-dipropionyloxy-1,4-pregnadiene-3,20-dione, mp 126° C.

EXAMPLE 4

(a) 10.0 g of 6$\alpha$-methylprednisolone is reacted analogously to Example 2a with 24 ml of the triethyl ester of orthobenzoic acid to obtain 17,21-(1-ethoxybenzylidenedioxy)-11$\beta$-hydroxy-6$\alpha$-methyl-1,4-pregnadiene-3,20-dione.

(b) The crude 17,21-(1-ethoxybenzylidenedioxy)-11$\beta$-hydroxy-6$\alpha$-methyl-1,4-pregnadiene-3,20-dione is hydrolyzed, worked up, and purified according to the conditions of Example 2b. Yield: 7.5 g of 17-benzoyloxy-11$\beta$,21-dihydroxy-6$\alpha$-methyl-1,4-pregnadiene-3,20-dione, mp 230° C.

(c) 1.9 g of 17-benzoyloxy-11$\beta$,21-dihydroxy-6$\alpha$-methyl-1,4-pregnadiene-3,20-dione is reacted, analogously to Example 2c, with acetic anhydride and worked up. The crude product is purified on 200 g of silica gel with a methylene chloride-acetone gradient (0–12% acetone), thus isolating 1.8 g of 21-acetoxy-17-benzoyloxy-11$\beta$-hydroxy-6$\alpha$-methyl-1,4-pregnadiene-3,20-dione, mp 258° C.

EXAMPLE 5

Under the conditions of Example 2c, 1.9 g of 17-benzoyloxy-11$\beta$,21-dihydroxy-6$\alpha$-methyl-1,4-pregnadiene-3,20-dione is reacted with propionic anhydride, worked up, and purified, thus obtaining 1.7 g of 17-benzoyloxy-11$\beta$-hydroxy-6$\alpha$-methyl-21-propionyloxy-1,4-pregnadiene-3,20-dione, mp 241° C.

EXAMPLE 6

0.9 g of 17-butyryloxy-11$\beta$,21-dihydroxy-6$\alpha$-methyl-1,4-pregnadiene-3,20-dione is reacted analogously to Example 2c with acetic anhydride and worked up. The crude product is purified on 40 g of silica gel with a methylene chloride-acetone gradient (0–12% acetone). Yield: 680 mg of 21-acetoxy-17-butyryloxy-11$\beta$-hydroxy-6$\alpha$-methyl-1,4-pregnadiene-3,20-dione, mp 158° C.

EXAMPLE 7

Under the conditions of Example 3, 0.8 g of 17-butyryloxy-11$\beta$,21-dihydroxy-6$\alpha$-methyl-1,4-pregnadiene-3,20-dione is reacted with propionic anhydride, worked up, and purified, yielding 775 mg of 17-butyryloxy-11$\beta$-hydroxy-6$\alpha$-methyl-21-propionyloxy-1,4-pregnadiene-3,20-dione, mp 126° C.

EXAMPLE 8

(a) Under argon at 0° C., 200 ml of a 5% solution of methyllithium in ether is added dropwise to a suspension of 36.5 g of copper(I) iodide in 730 ml of anhydrous tetrahydrofuran. The yellow solution is cooled to −30° C., and a solution of 29.0 g of 11$\beta$,17-dihydroxy-21-isovaleryloxy-6$\alpha$-methyl-1,4-pregnadiene-3,20-dione in 730 ml of anhydrous tetrahydrofuran is added thereto. The mixture is stirred further for 10 minutes at −25° C. and poured onto an aqueous ammonium chloride solution. After extraction with methylene chloride, the organic solution is washed, dried over sodium sulfate, and evaporated under vacuum. The crude product is purified on 750 g of silica gel with a methylene chloride-acetone gradient (0–20% acetone), yielding 18.2 g of 11β,21-dihydroxy-17-isovaleryloxy-6α-methyl-1,4-pregnadiene-3,20-dione, mp 164° C.

(b) Analogously to Example 2c, 1.5 g of 11β,21-dihydroxy-17-isovaleryloxy-6α-methyl-1,4-pregnadiene-3,20-dione is reacted in 15 ml of pyridine with 7.5 ml of acetic anhydride, worked up, and purified, thus isolating 980 mg of 21-acetoxy-11β-hydroxy-6α-methyl-17-isovaleryloxy-1,4-pregnadiene-3,20-dione, mp 172° C.

EXAMPLE 9

(a) Under the conditions of Example 8a, 3.6 g of 11β,17-dihydroxy-6α-methyl-21-trimethylacetoxy-1,4-pregnadiene-3,20-dione is rearranged to 780 mg of 11β,21-dihydroxy-6α-methyl-17-trimethylacetoxy-1,4-pregnadiene-3,20-dione, worked up, and purified.

(b) As described in Example 2c, 700 mg of 11β,21-dihydroxy-6α-methyl-17-trimethylacetoxy-1,4-pregnadiene-3,20-dione is reacted with acetic anhydride and worked up. Yield: 610 mg of 21-acetoxy-11β-hydroxy-6α-methyl-17-trimethylacetoxy-1,4-pregnadiene-3,20-dione, mp 201° C.

EXAMPLE 10

(a) Analogously to Example 8a, 2.0 g of 11β,17-dihydroxy-6α-methyl-21-valeryloxy-1,4-pregnadiene-3,20-dione is rearranged with lithium dimethyl cuprate into 1.8 g of 11β,21-dihydroxy-6α-methyl-17-valeryloxy-1,4-pregnadiene-3,20-dione, worked up, and purified.

(b) 1.5 g of 11β,21-dihydroxy-6α-methyl-17-valeryloxy-1,4-pregnadiene-3,20-dione is acetylated analogously to Example 2c with acetic anhydride to 1.2 g of 21-acetoxy-11β-hydroxy-6α-methyl-17-valeryloxy-1,4-pregnadiene-3,20-dione.

EXAMPLE 11

(a) 2.0 g of 11β,17-dihydroxy-21-isobutyryloxy-6α-methyl-1,4-pregnadiene-3,20-dione is rearranged analogously to Example 8a into 1.3 g of 11β,21-dihydroxy-17-isobutyryloxy-6α-methyl-1,4-pregnadiene-3,20-dione.

(b) 1.0 g of 11β,21-dihydroxy-17-isobutyryloxy-6α-methyl-1,4-pregnadiene-3,20-dione is reacted analogously to Example 2c with acetic anhydride to 0.7 g of 21-acetoxy-11β-hydroxy-17-isobutyryloxy-6α-methyl-1,4-pregnadiene-3,20-dione, worked up, and purified.

EXAMPLE 12

Under the conditions of Example 2c, 1.0 g of 11β,21-dihydroxy-6α-methyl-17-propionyloxy-1,4-pregnadiene-3,20-dione is reacted with isobutyric anhydride, worked up, and purified, yielding 850 mg of 11β-hydroxy-21-isobutyryloxy-6α-methyl-17-propionyloxy-1,4-pregnadiene-3,20-dione.

EXAMPLE 13

1.0 g of 11β,21-dihydroxy-6α-methyl-17-propionyloxy-1,4-pregnadiene-3,20-dione is reacted in pyridine with 5 ml of valeric anhydride as described in Example 2c. After the usual working-up process and purification on 50 g of silica gel with a methylene chloride-acetone gradient (0–15% acetone), 960 mg of 11β-hydroxy-6α-methyl-17-propionyloxy-21-valeryloxy-1,4-pregnadiene-3,20-dione is isolated.

EXAMPLE 14

Under the conditions of Example 2c, 1.0 g of 17-butyryloxy-11β,21-dihydroxy-6α-methyl-1,4-pregnadiene-3,20-dione is reacted with butyric anhydride and worked up analogously. The crude product is recrystallized from acetone/hexane, thus isolating 820 mg of 17,21-dibutyryloxy-11β-hydroxy-6α-methyl-1,4-pregnadiene-3,20-dione.

EXAMPLE 15

(a) A solution of 5.0 g of 21-acetoxy-11β,17-dihydroxy-6α-methyl-1,4-pregnadiene-3,20-dione in 25 ml of pyridine is combined at −15° C. dropwise with 3 ml of trifluoroacetic anhydride and stirred for 10 minutes at −10° C. The mixture is poured onto an ice water-sodium chloride solution and the precipitate filtered off. The residue is taken up in methylene chloride, washed neutral and, after drying over sodium sulfate, concentrated under vacuum. Yield: 5.4 g of 21-acetoxy-17-hydroxy-6α-methyl-11β-trifluoroacetoxy-1,4-pregnadiene-3,20-dione.

(b) 4.0 g of the crude product obtained in (a) is stirred in 50 ml of diethylene glycol dimethyl ether and 6.0 ml of propionic anhydride with 6.5 g of 4-dimethylaminopyridine for 18 hours at room temperature. After working up the reaction mixture as usual, 4.5 g of 21-acetoxy-6α-methyl-17-propionyloxy-11β-trifluoroacetoxy-1,4-pregnadiene-3,20-dione is isolated.

(c) 3.5 g of 21-acetoxy-6α-methyl-17-propionyloxy-11β-trifluoroacetoxy-1,4-pregnadiene-3,20-dione is stirred in 80 ml of methanol and 4.2 ml of triethylamine for 4 hours at room temperature. The crude product is purified on 600 g of silica gel with a methylene chloride-acetone gradient (0–15% acetone), thus isolating 2.3 g of 21-acetoxy-11β-hydroxy-6α-methyl-17-propionyloxy-1,4-pregnadiene-3,20-dione.

EXAMPLE 16

A sweetwort tube slant with Curvularia lunata NRRL 2380, age 7–14 days, is floated away with 3 ml of physiological sodium chloride solution, and used for inoculating a 2-liter Erlenmeyer flask containing 500 ml of a nutrient solution, sterilized for 30 minutes at 120° C. in an autoclave, made up of 2% glucose and 2% corn steep liquor, adjusted to pH 6.5. After 60 hours of shaking on a rotary shaker (165 rpm) at 30° C., 250 ml of this germination culture servesfor inoculating the preliminary fermentor.

A 20-liter preliminary fermentor, charged with 15 l of a nutrient medium, sterilized at 121° C. and 1.1 atm. gauge and having the same composition as the germination medium, is inoculated with 250 ml of germination culture. With the addition of silicone SH as the defrother, the germination is then conducted at 29° C. and 0.7 atm. gauge under aeration (15 l/min) and agitation (220 rpm) for 24 hours. 1.5 liters of this preliminary fermentor culture serve for inoculation of the main fermentor.

A 20-liter main fermentor, filled with 13.5 l of a sterilized nutrient medium made up of 3% corn steep liquor and 0.7% glucose, adjusted to pH 5.5, is inoculated with 1.5 l of preliminary fermentor culture. After an incubating phase of 12 hours under preliminary fermentor conditions, a sterilized solution of 12.18 g of 17,21-(1-methoxyethylidenedioxy)-6α-methyl-4-pregnene-3,20-dione in 130 ml of dimethylformamide is added thereto, and the mixture is further stirred and aerated. Four hours after addition of the substrate the pH of the culture broth is set to 4.5 and maintained at this value ±pH 0.2 by automatic control with 16% NaOH/20% $H_2SO_4$ until the end of the hydroxylation (51 hours contact period).

After the hydroxylation has been completed, half of the culture volume (6.5 l) is transferred into a second, sterilized fermentor, and both cultures are combined with respectively the same amount by volume (6.5 l) of an Arthrobacter simplex culture ATCC 6946, grown in the meantime with a germination period of 24 hours. The pH is then adjusted to 5.5 and maintained at this value by automatic control, as in the first fermentation stage, until the end of the conversion. After 22 hours of contact with the Arthrobacter culture, the dehydrogenation is completed.

For working-up purposes, the content of the fermentor is filtered, and the culture filtrate as well as the filtered-off mycelium are extracted separately with methyl isobutyl ketone. The extracts are combined and first concentrated in a forced circulation evaporator at about 40° C. under vacuum to one liter whereafter the mixture is concentrated completely to dryness in a 2-liter round flask on a forced circulation evaporator under vacuum at a bath temperature of 40° C. The remaining, oily residue is combined with 400 ml of hexane, briefly shaken, and the washing hexane, containing silicone oil and lipids, is decanted. Subsequently the residue is again combined with 400 ml of hexane and stirred for 2 hours with the use of a laboratory-scale magnetic stirrer. The residue, now completely crystallized, is vacuum-filtered, washed with 100 ml of hexane, and dried in a vacuum drying cabinet for 4 hours at 60° C., thus obtaining crystalline 17-acetoxy-11β,21-dihydroxy-6α-methyl-1,4-pregnadiene-3,20-dione, mp 198°–201° C., in a yield of 78% of theory.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. 21-Acetoxy-11β-hydroxy-6α-methyl-17-propionyloxy-1,4-prenadiene-3,20-dione.

2. A 6α-methylprednisolone derivative of the formula

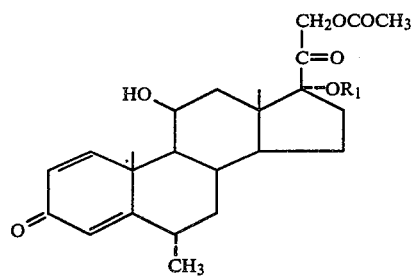

wherein
R₁ is C₃₋₆-alkanoyl or benzoyl.

3. 21-Acetoxy-11β-hydroxy-17-isobutyryloxy-6α-methyl-1,4-pregnadiene-3,20-dione, a compound of claim 2.

4. 21-Acetoxy-11β-hydroxy-6α-methyl-17-trimethylacetoxy-1,4-pregnadiene, 3,20-dione, a compound of claim 2.

5. 21-Acetoxy-17-butyryloxy-11β-hydroxy-6α-methyl-1,4-pregnadiene-3,2-dione, a compound of claim 2.

6. 21-Acetoxy-11β-hydroxy-6α-methyl-17-isovaleryloxy-1,4-pregnadiene-3,20-dione, a compound of claim 2.

7. 21-Acetoxy-11β-hydroxy-6α-methyl-17-valeryloxy-1,4-pregnadiene-3,20-dione, a compound of claim 2.

8. 21-Acetoxy-17-benzoyloxy-11β-hydroxy-6α-methyl-1,4-pregnadiene-3,20-dione, a compound of claim 2.

9. A pharmaceutical composition for topical administration comprising a topically antiinflammatorily effective amount of a compound of claim 1 and a pharmaceutically acceptable carrier for topically administrable pharmaceutical compositions.

10. A pharmaceutical composition for topical administration comprising a topically antiinflammatorily effective amount of a compound of claim 2 and a pharmaceutically acceptable carrier for topically administrable pharmaceutical compositions.

11. A method of topically treating inflammation in a patient in need of such treatment comprising administering to the patient an effective amount of a composition of claim 9.

12. A method of topically treating inflammation in a patient in need of such treatment comprising administering to the patient an effective amount of a composition of claim 10.

13. A method of treating an allergic disease of the intestinal tract in a patient in need of such treatment comprising administering to the patient an amount of a compound of claim 1 effective for such treatment.

14. A method of treating an allergic disease of the intestinal tract in a patient in need of such treatment comprising adminstering to the patient an amount of a compound of claim 2 effective for such treatment.

* * * * *